(12) United States Patent
Nikou et al.

(10) Patent No.: US 11,669,232 B2
(45) Date of Patent: Jun. 6, 2023

(54) SYSTEMS AND METHODS FOR DETERMINING A POSITION FOR PLACING OF A JOINT PROSTHESIS

(71) Applicant: Blue Belt Technologies, Inc., Plymouth, MN (US)

(72) Inventors: Constantinos Nikou, Monroeville, PA (US); Branislav Jaramaz, Pittsburgh, PA (US)

(73) Assignee: Blue Belt Technologies, Inc., Memphis, TN (US)

(*) Notice: Subject to any disclaimer, the term of this patent is extended or adjusted under 35 U.S.C. 154(b) by 0 days.

(21) Appl. No.: 17/512,948

(22) Filed: Oct. 28, 2021

(65) Prior Publication Data

US 2022/0050581 A1 Feb. 17, 2022

Related U.S. Application Data

(63) Continuation of application No. 16/103,315, filed on Aug. 14, 2018, now Pat. No. 11,188,204, which is a continuation of application No. 14/187,940, filed on Feb. 24, 2014, now Pat. No. 10,452,238.

(Continued)

(51) Int. Cl.
G06F 3/0484 (2022.01)
A61B 34/10 (2016.01)
(Continued)

(52) U.S. Cl.
CPC .......... *G06F 3/04842* (2013.01); *A61B 34/10* (2016.02); *G06F 3/04815* (2013.01); *A61B 2034/104* (2016.02)

(58) Field of Classification Search
CPC ......... G06F 19/34; G06F 17/50; A61B 34/10; A61B 2034/101; A61B 2034/107;
(Continued)

(56) References Cited

U.S. PATENT DOCUMENTS 5,682,886 A * 11/1997 Delp .................... A61B 90/36
600/407
8,831,302 B2 * 9/2014 Mahfouz ............... A61F 2/4657
382/128

(Continued)

FOREIGN PATENT DOCUMENTS

EP 2373244 A1 * 10/2011 ............. A61B 34/10
WO WO-2010068212 A1 * 6/2010 ............. A61B 34/10
WO WO-2012112694 A2 * 8/2012 ........... A61B 17/154

*Primary Examiner* — Yongjia Pan
(74) *Attorney, Agent, or Firm* — DLA Piper LLP

(57) ABSTRACT

Systems and methods for virtual implant placement to implement joint gap planning are discussed. For example, a method can include operations for receiving a first implant parameter set based on a surgical plan that was generated while moving the joint through a range of motion. The method can include generating a first set of candidate implant parameter sets that are the result of an incremental change, relative to the first implant parameter set, to at least one parameter of the first parameter set. The method can include calculating a result for at least one candidate implant parameter set and providing a graphical representation of the result according to at least one candidate implant parameter set. The result can be color-coded to correlate to a candidate implant parameter set. The display can include color-coded user interface controls to allow a user to execute incremental changes corresponding to candidate implant parameter sets.

22 Claims, 6 Drawing Sheets

Related U.S. Application Data

(60) Provisional application No. 61/791,829, filed on Mar. 15, 2013.

(51) Int. Cl.
   *G06F 3/04842* (2022.01)
   *G06F 3/04815* (2022.01)

(58) Field of Classification Search
   CPC ............ A61B 2034/2068; A61B 34/25; A61B 2034/252; A61B 17/154; A61B 2034/105; A61B 2034/108; A61F 2/38; A61F 2/30942
   See application file for complete search history.

(56) References Cited

U.S. PATENT DOCUMENTS

| | | | |
|---|---|---|---|
| 9,456,765 B2* | 10/2016 | Odermatt | A61B 5/4528 |
| 9,827,051 B2* | 11/2017 | Arata | A61F 2/389 |
| 9,913,692 B2* | 3/2018 | Arata | A61F 2/389 |
| 2005/0182320 A1* | 8/2005 | Stiffer | A61B 5/1127 600/429 |
| 2008/0262812 A1* | 10/2008 | Arata | A61B 90/36 703/11 |
| 2008/0319448 A1* | 12/2008 | Lavallee | G06F 30/00 703/11 |
| 2009/0209884 A1* | 8/2009 | Van Vorhis | G16H 50/50 600/595 |
| 2010/0332194 A1* | 12/2010 | McGuan | G09B 23/30 703/11 |
| 2011/0066245 A1* | 3/2011 | Lang | A61F 2/38 623/18.11 |
| 2013/0144352 A1* | 6/2013 | Axelson, Jr. | A61B 34/10 606/86 R |
| 2014/0188240 A1* | 7/2014 | Lang | A61F 2/3662 29/592 |
| 2014/0189508 A1* | 7/2014 | Granchi | A61B 34/25 715/705 |

\* cited by examiner

SYSTEMS AND METHODS FOR DETERMINING A POSITION FOR PLACING OF A JOINT PROSTHESIS

RELATED APPLICATIONS

This patent application is a continuation application of U.S. patent application Ser. No. 16/103,315, filed on Aug. 14, 2018, titled "Systems and Methods for Determining a Position for Placing of a Joint Prosthesis," which is a continuation application of U.S. patent application Ser. No. 14/187,940, filed on Feb. 24, 2014, titled "Systems and Methods for Determining a Position for Placing of a Joint Prosthesis," and issued as U.S. Pat. No. 10,452,238, which claims the benefit of priority to U.S. Provisional Patent Application Ser. No. 61/791,829, filed on Mar. 15, 2013, each of which is hereby incorporated by reference herein in its entirety.

TECHNICAL FIELD

This application relates generally to computer-aided surgical procedures, and more specifically to systems and methods to provide computer-aided placement planning for joint replacement implants.

BACKGROUND

In knee replacement surgery, a surgeon places a first prosthesis on the distal end of the femur and a second prosthesis at the proximal end of the tibia. A surgeon should place the prostheses in an optimal way with respect to various parameters, for example, with respect to the gap between the prostheses throughout a range of motion. For example, if the gap between the tibia and femur is too small at any time during motion, the patient can experience painful binding. On the other hand, if the gap is too large, the knee joint can be too loose and become unstable.

Determining an optimal position and orientation of these prostheses, or implants, relative to the patient is difficult. Many factors must be taken into account—some quantitative, other qualitative. So called "surgical navigation" systems can help quantify certain plan parameters with high accuracy, but it is still up to the surgeon to balance these and other parameters, incrementally adjusting the plan often with a simple user interface. The user interface must be simple to use in the operating room, and therefore all the ramifications of any particular decision by the surgeon cannot be presentable easily without a complex interface. Medical personnel can use the surgical navigation system's computer to optimize the quantitative parameters, though it cannot know what the surgeon is thinking, and it cannot evaluate the qualitative parameters. In addition, two or more potential surgical plans can be equivalent when evaluated per the qualitative metrics, but it would require a surgeon to choose between these alternatives in light of the qualitative factors. The mental task of predicting the outcome of desired changes to the plan that are available via the user interface with respect to both the qualitative and quantitative metrics is a difficult one.

In light of this challenge, there exists a general need to provide a surgeon with easy to evaluate predicted results of various actions, and to allow the surgeon to choose one or more actions that can result in an improved placement of the implant on one or both of a femur and a tibia.

BRIEF DESCRIPTION OF THE DRAWINGS

Some embodiments are illustrated by way of example and not limitation in the figures of the accompanying drawings in which.

DEFINITIONS

Figure 1:
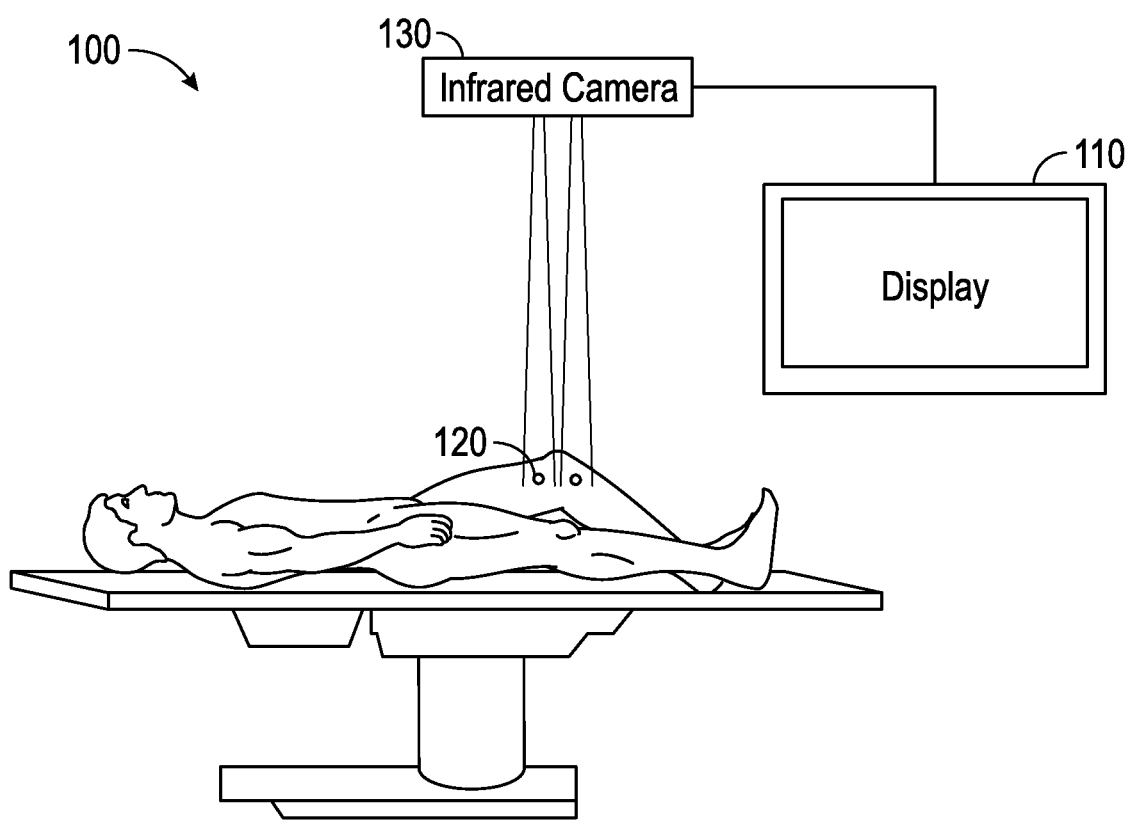
FIG. 1 is a block diagram depicting a system for providing joint gap planning through virtual placement of a prosthetic implant, according to an example embodiment.

Implant—For the purposes of this specification and the associated claims, the term "implant" is used to refer to a prosthetic device or structure manufactured to replace or enhance a biological structure. For example, in a knee replacement procedure an implant can be placed on one or both of the tibia and the femur. While the term "implant" is generally considered to denote a man-made structure (as contrasted with a transplant), for the purposes of this specification an implant can include a biological tissue or material transplanted to replace or enhance a biological structure.

Implant host—For the purposes of this specification and the associated claims, the term "implant host" is used to refer to a patient. In certain instances, the term implant host can refer, more specifically, to a particular joint or location of the intended implant within a particular patient's anatomy. For example, in a knee replacement procedure the implant host can refer to the knee joint of the patient being replaced, partially replaced, or repaired.

Real-time—For the purposes of this specification and the associated claims, the term "real-time" is used to refer to calculations or operations performed on-the-fly as events occur or input is received by the operable system. However, the use of the term "real-time" is not intended to preclude operations that cause some latency between input and response, so long as the latency is an unintended consequence induced by the performance characteristics of the machine.

DETAILED DESCRIPTION

This disclosure describes example systems and methods of guiding a surgeon toward an optimal the placement of prosthetic implants relative to the bones of a joint. In the following description, for purposes of explanation, numerous specific details are set forth in order to provide a thorough understanding of example embodiments. It will be evident, however, to one skilled in the art, that embodiments can be practiced without these specific details.

When a surgeon places a prosthetic implant in a joint, the surgeon can place one portion of an implant at a first bone in the joint and a second portion of the implant at a second bone of the joint. For example, in the case of a knee prosthesis, the surgeon may place one implant at a tibia and a second implant at a femur. When placing the implants, it is important to ensure a certain amount of gap between the implants through a range of motion in the knee. An implant with too little of a gap can cause pain to the patient or can affect the full range of motion or operation of the joint after the implant is in place. However, if there is too much gap the joint may become unstable.

Accordingly, gap planning is important to ensure that there is neither too much nor too little gap between bones in the joint once the prosthetic implant is in place. Computer systems may provide automated gap planning but fully-automated systems may prevent application of human judgment to the implant planning process. Therefore, some embodiments provide a computer-aided gap-planning process that allows a surgeon to install virtual prosthetic implants at different positions and to visualize the manner in which changes to placement of the prosthetic implants will cause changes to the gap between bones in the joint.

FIG. 1 is a block diagram depicting a system 100 for providing joint gap planning through virtual placement of a prosthetic implant, according to an example embodiment. In an example, a patient will lie on an operating table 105. A computer system 110 will provide a display for viewing data provided by optical trackers 120 and an infrared camera system 130. The optical trackers 120 and infrared camera system 130 can provide data relevant to, for example, a knee joint. In an example, the infrared cameras system 130 can detect tracking spheres located on the optical trackers 120. Location data can be extracted from the images of the optical trackers 120 to provide location data relative to the patient and more specifically the joint on which the procedure is to be performed.

Figure 2:
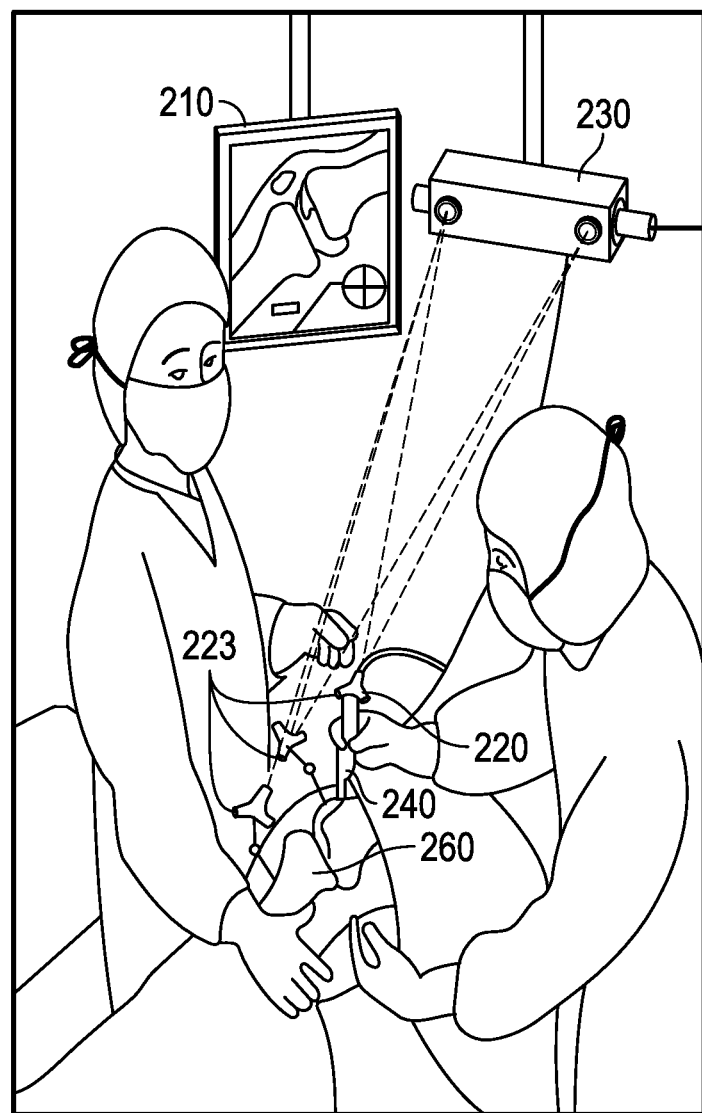
FIG. 2 illustrates an exemplary optical surgical navigation setup according to an example embodiment.

FIG. 2 illustrates an exemplary optical surgical navigation setup. An infrared camera 230 and optical tracker 220 can be used to perform surgical navigation. The optical trackers 120 can be rigidly attached to any object 240 that the surgeon wishes to track during the surgical procedure. The optical trackers 220 can serve functions of the optical trackers 120 (FIG. 1). The infrared camera 230 can serve functions of the infrared camera system 130 (FIG. 1).

The infrared camera 230 can take continuous images of the workspace during the surgical procedure, and the markers 225 are detected from those pictures. Using the known rigid spatial relationship of the markers 225 on the image frame, the position of the object 240 in a three-dimensional space can be determined. The object 240 location can be continuously output to the display 210. The display 210 can also continuously display the object 240 location relative to the patient anatomy. The known position of the object can serve to register a set of anatomic landmarks that are understood by the system to define an anatomically based coordinate system. This system can describe anatomic directions relative to the implant host, such as "left", "right", "superior" (up), and "anterior" (to the front). Registration of these landmarks to an anatomic coordinate system is well understood by those skilled in the art of orthopedic surgical navigation. More advanced registrations, such as registration to preoperatively attainted medical images, such as computed tomography or CT, is also evident to those skilled in the art.

Figure 3A:
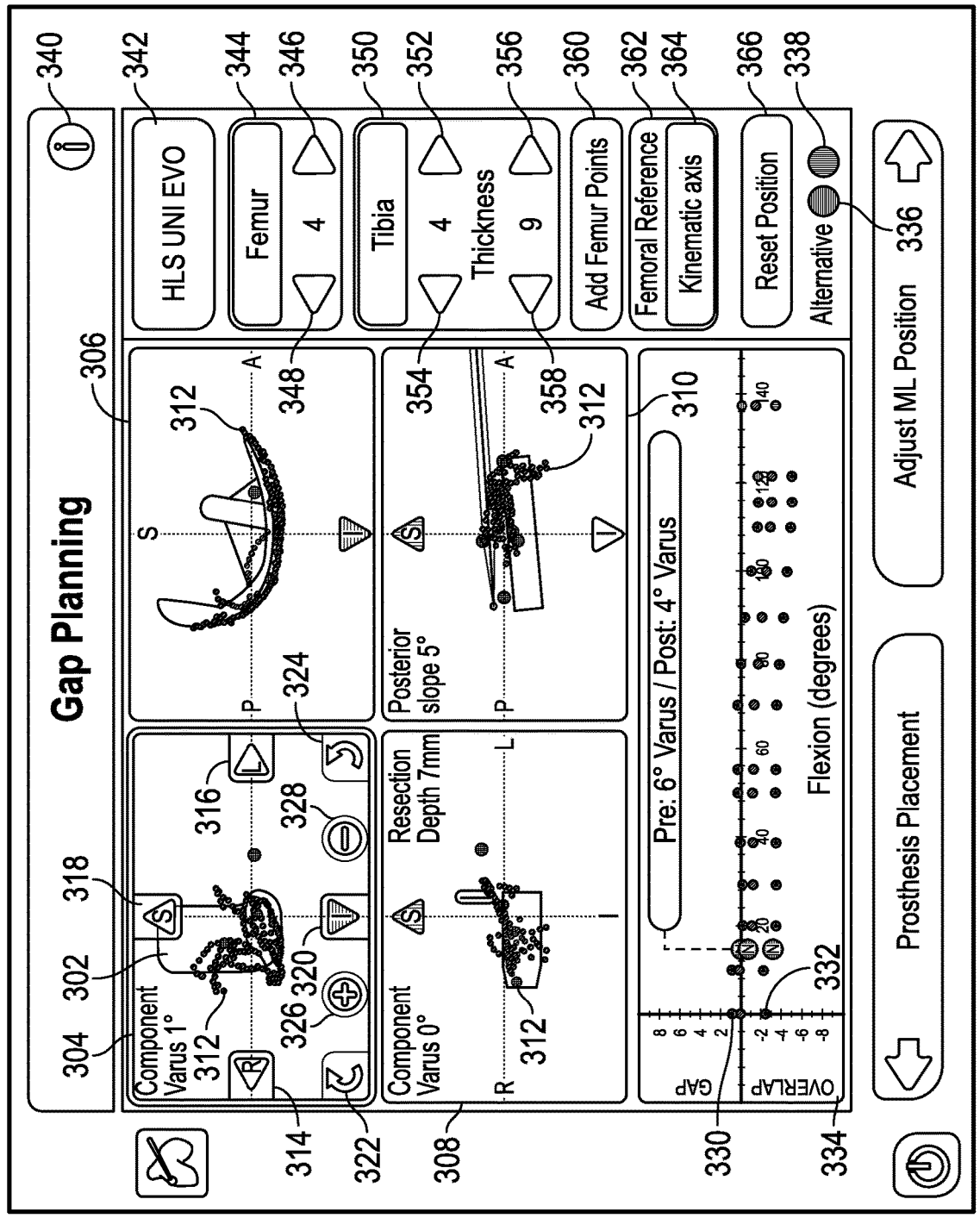
FIG. 3A is a diagram of a gap planning user interface, according to an example embodiment.

FIG. 3A is a diagram of a gap planning user interface 300, according to an example embodiment, that can be displayed using the computing system 110 (FIG. 1) or 210 (FIG. 2). Through visualization and controls on the user interface 300, a surgeon can select from two or more options for moving a virtual implant relative to one or more of the subject bones.

The surgeon can view in advance the effect that each of the candidate options for movement will have on the joint gap at various points in the range of motion of the joint. In this manner, the surgeon can incrementally change implant locations to arrive at an optimized gap curve.

Before the virtual implant placement described herein, the surgeon or technician can have recorded the motion of the leg, for example the motion of the bones of the knee joint, through a range of motion of the joint. However, embodiments are not limited thereto. The graph depiction 334, hereinafter a "gap curve," can be a replaying of that recorded motion, but with the virtual implants in place. The graph therefore can depict how the virtual implants interact with each other in those recorded positions. For example, a gap curve can show the surgeon how the gap between the tibia and femur changes with each degree of flexion of the joint. An overlap represents a measure of the degree to which the virtual implants will cause the tibia and femur to overlap (e.g., a "negative gap").

Figure 3B:
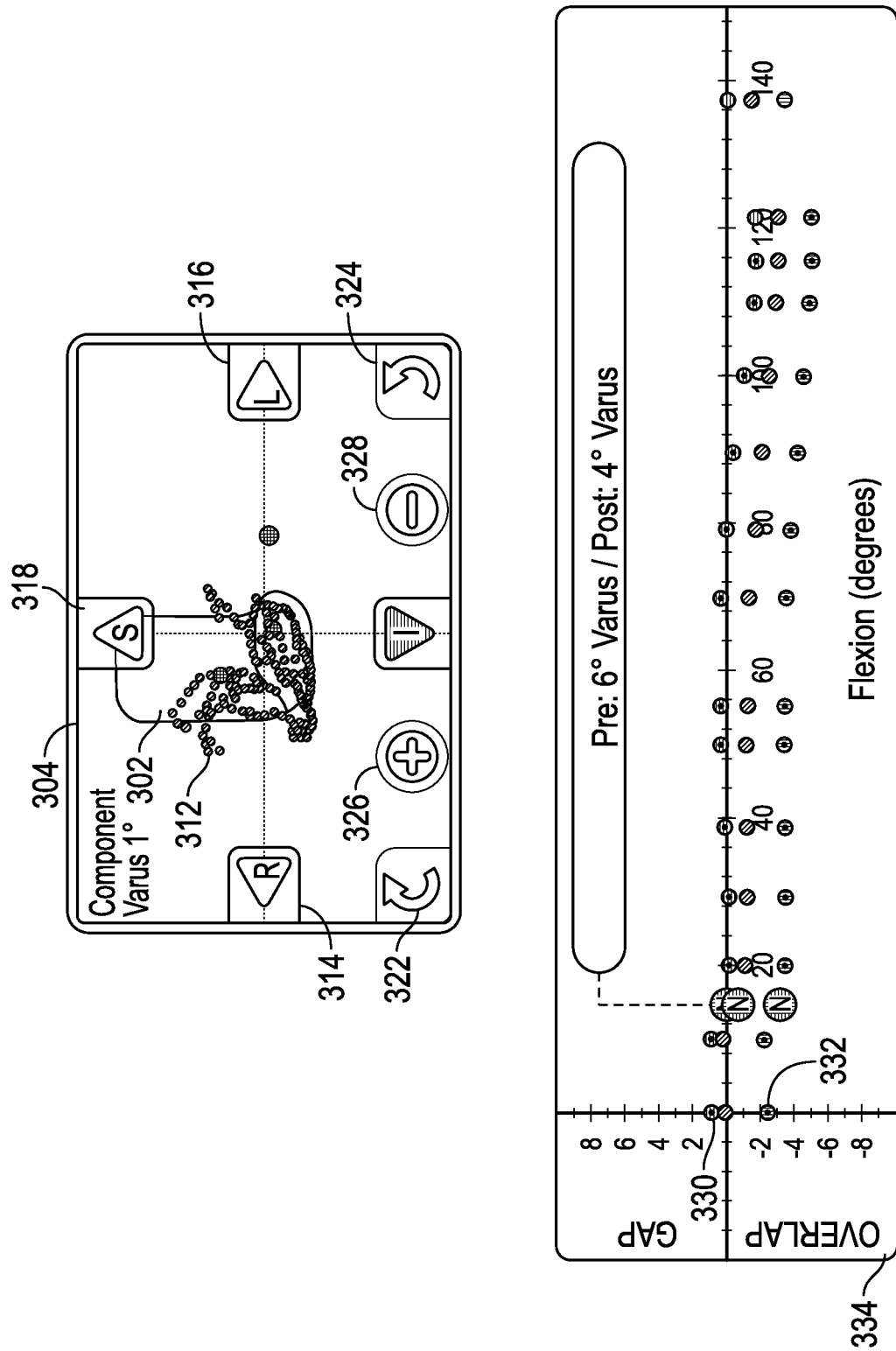
FIG. 3B includes an enlarged depiction of a quadrant, gap curves, and graph described regarding FIG. 3A according to an example embodiment.

The user interface 300 of FIG. 3A depicts gap planning with views of a femoral implant 302. Some embodiments can include a same or at least somewhat similar user interface that includes views of a tibia (not shown in 3A), for virtual placement of an implant on the tibia. Each quadrant 304, 306, 308, and 310 of the display can depict a different view of the femoral implant 302. FIG. 3B includes an enlarged depiction of a quadrant 304, gap curves 330 and 332, and the graph 334 described herein regarding FIG. 3A.

These views can be aligned with the anatomic coordinate systems so the relative placements of the implants in these views can be correlated to adjustments in the surgical plan that the surgeon better understands, such as movement of the implant "to the anterior". The locations of the bone relative to the sensors are mapped by points 312 in the quadrant views 304, 306, 308, and 310. The locations of a target bone can also be used as inputs to functions described herein. In the illustrative example, the upper left quadrant 304 can include four arrows 314, 316, 318 and 320. The left (L) and right (R) 316 and 314 can be buttons for virtually moving the implant anatomically right and left, respectively. The up arrow and down arrow 318 and 320 can be buttons for virtually moving the implant superior (S) anatomically to its current position or inferior (I) to its current position, respectively. The upper right quadrant 306 can depict another view of the femoral implant 302 with a current position 312 of the bone relative to the sensors. In addition to inferior and superior movements, the upper right quadrant can provide controls (not shown in FIG. 3A) for moving the virtual implant in a posterior (P) or anterior (A) direction. Rotation buttons, for example the two rotation buttons 322 and 324 shown in the upper left quadrant 304, can allow the surgeon to rotate the implants virtually. Zooming buttons 326 and 328 can allow the surgeon to zoom the view in or out.

Taken alone, the interface described above allows the surgeon to manipulate the positions of the implants relative to their host bones. However, it can be difficult for the surgeon to know which direction to move the implants to result, for example, in a "better" gap curve. Therefore, the system can further evaluate some or all of the adjustments available in the user interface as candidate new positions. The system can then apply (in the example above) a heuristic function to the data that makes up the gap curve for each candidate parameter, and select at least two of these adjustments as representing next best incremental movements of the implant, such as femoral implant 302. In an example, the user interface 300 can color code the representative gap curves and the corresponding controls, such as 314, 316, 318, or 320, that the surgeon would manipulate to achieve the new gap curve.

The result of these candidate motions can be depicted as predicted gap curves 330 and 332 in the graph 334 along the bottom of the example display. FIG. 3B illustrates an enlarge view of predicted gap curves 330 and 332 in the graph 334. The resulting gap curves 330 and 332 can be color-coded in some embodiments to correspond to their candidate motions shown in the quadrants 304, 306, 308 and 310. For example, moving the implant in a superior (S) direction can create a gap curve 330. Moving the implant in an inferior (I) direction can create a gap curve 332. These allow the surgeon to appreciate quickly the effects of those candidate motions that likely affect the gap curve in a preferable way. This allows the surgeon to focus more attention on more qualitative factors, such as the fit of the implant surface to the native bone shape.

Furthermore, the color-coded Alternative buttons 336 and 338 to the right of the gap curve 334 can allow the surgeon to implement movements of the virtual implant to create, in one movement, the corresponding color-coded gap curve. For example, clicking the alternative button 336 can result in the implants being placed to create the gap curve 330. A surgeon can choose the Alternative buttons 336 or 338 when, for example, the surgeon has decided that the gap curve 330 or 332 is optimal or nearly optimal based on the surgeon's own professional opinion or on other criteria.

Other user interface elements can be provided. A help button 340 can be provided to provide online guidance to the surgeon. The Femur button 344 can be used to select the current model, for example, the button can be used to select planning of the femur or tibial implant. Therefore, the user interface can be changed to display a tibia for planning of a tibial implant. The thickness of the displayed femoral implant 302 can be changed using buttons 346 or 348. The Tibia menu 350 can be used to change the thickness of a tibia using buttons 352, 354, 356, and 358. The Add Femur Points button 360 can be used to add more points 312 on the displayed bone. The Femoral Reference box 362 can display the current femoral reference being used. Pressing the button 364, herein captioned "kinematic axis," can display a menu of other available femoral references. The Reset position button 366 can reset the implant position to the implant position's default position.

The computing system 110, according to example embodiments, can simulate one or all of the surgeon's incremental movements of the virtual implants to calculate one or more candidate movements for presenting to the surgeon for subsequent selections. A subsequent set of candidate parameters can then be presented to the surgeon, and the surgeon can view a preview of a second set of gap curves that would result from any or all of the candidate movements.

The subsequent set of candidate positions can be presented in the same or different quadrant views, with the same or different candidate control options. For example, a subsequent set of candidate positions may not present a superior movement or an anterior movement alternative to the surgeon, at least potentially indicating that such movements would place the implant out of tolerances or guidelines. Alternatively, a subsequent set of candidate positions can present a superior movement alternative but not present an inferior movement alternative. The surgeon can iteratively select candidate positions, view resulting gap curves, and be presented with further sets of candidate positions and gap curves, until the surgeon is satisfied with a gap curve.

When the surgeon is satisfied with a gap curve, the surgeon can surgically implant a femoral implant, a tibial implant, or both a femoral implant and a tibial implant, to create the simulated gap curve in the actual knee joint of the patient. Additionally, when the surgeon is satisfied with the gap curve, a surgical plan for implementation with a semi-active robotic surgical cutting instrument can be developed. The surgical plan can include graphical illustrations of at least a portion of the patients anatomy color-coded to indicate what portion of the depicted anatomy needs to be altered (e.g., cut).

In example embodiments, therefore, a surgeon can be permitted to focus on the desire to move the gap curve in a particular way, and be presented with computer-analyzed suggestions for incremental candidate movements that can create such a gap curve more quickly, without giving up his autonomy or decision-making powers and while still allowing the surgeon to consider other factors not displayable on a plot.

Example embodiments can aid a surgeon faced with the opportunity to perform a number of actions with an implant, for example adjustments to the position, orientation, size, or other properties or parameters relevant to the implant. It can be overwhelming to a surgeon to understand the complicated interactions of how each movement would affect the gap curve. Example embodiments therefore provide a "betterness function," to guide the surgeon with implant movements or adjustments.

Example Methods

Figure 4:
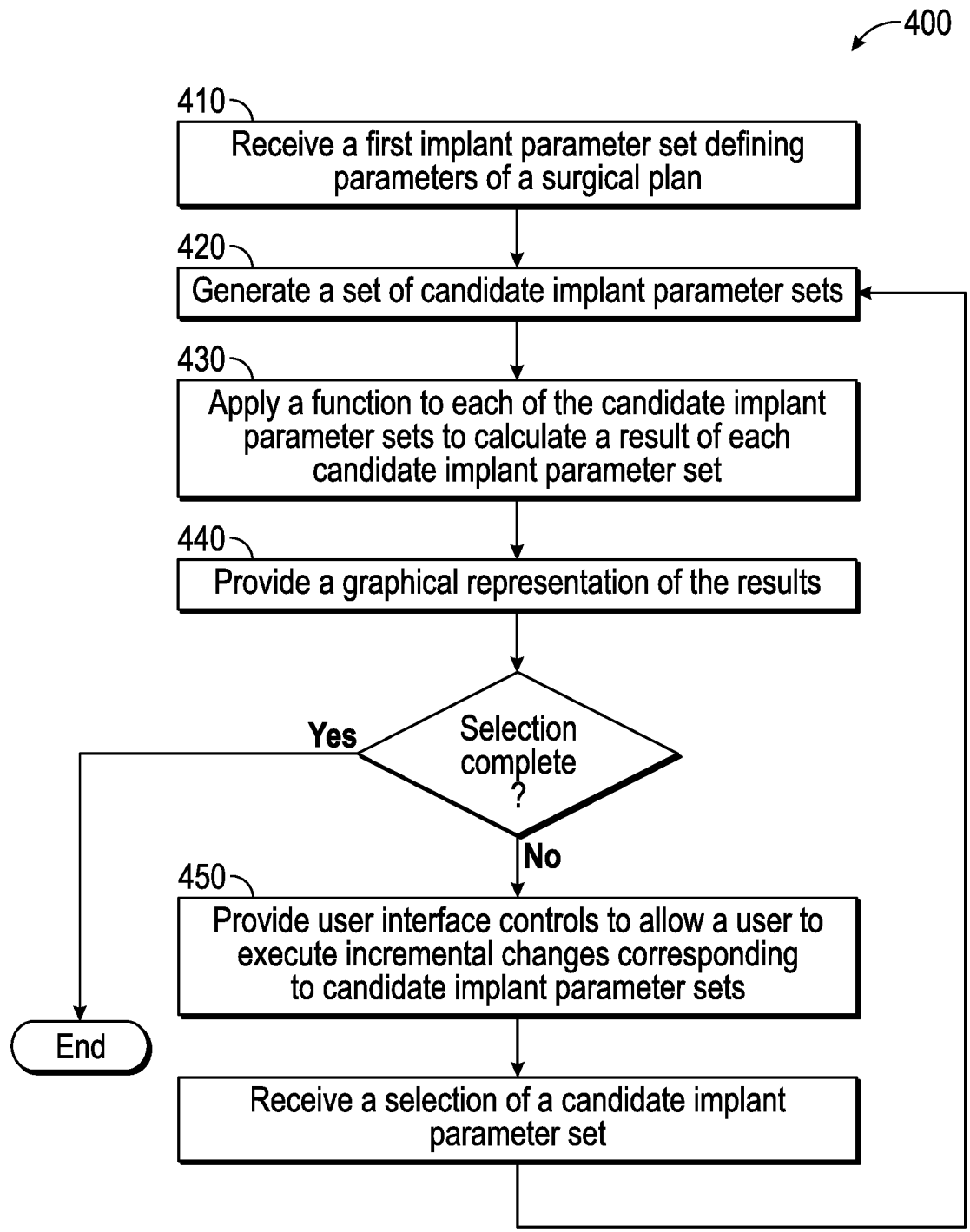
FIG. 4 is a flowchart illustrating a method for gap planning, according to an example embodiment.

FIG. 4 is a flowchart illustrating a method 400 for gap planning, according to an example embodiment. In operation 410, the computing system 110 (FIG. 1) can receive a first (e.g., initial) implant parameter set. The first implant parameter set can define parameters of a surgical plan. The surgical plan can be previously generated using data collected while moving the joint through a range of motion. However, embodiments are not limited thereto. The joint can be a knee joint although embodiments are not limited thereto.

The computing system 110 can generate and display an initial gap curve based on gap data collected while moving the joint through the range of motion. The first implant parameter set can include one or more of a size of an implant, a shape of the implant, an orientation of the implant, and a position of the implant relative to the joint. The computing system 110 can generate and display a virtual three-dimensional model of the joint for using in the planning process, and the computing system 110 can generate and display an initial implant location based at least in part on the virtual three-dimensional model and on the first implant parameter set.

The target bone model can include a medical image, a point cloud, a parametric model, or other morphological description of the target bone. The medical images can include two-dimensional (2D) or three-dimensional (3D) images. Examples of the medical images include an X-ray, an ultrasound image, a computed tomography (CT) scan, a magnetic resonance (MR) image, a positron emission tomography (PET) image, a single-photon emission computed tomography (SPECT) image, or an arthrogram. The target bone model can include shape data, appearance data, or data representing other morphological characteristics of the target bone surface. The shape data may include geometric characteristics of a bone such as landmarks, surfaces, boundaries of 3D images objections. The appearance data may include both geometric characteristics and intensity information of a bone.

In operation 420, the computing system 110 can generate a first set of candidate implant parameter sets. An implant parameter set can include, for example, a size of an implant, a shape of the implant, an orientation of the implant, and a position of the implant relative to the joint. Each candidate parameter set will be the result of an incremental change, relative to the first implant parameter set, to at least one parameter of the first parameter set. The increments of these incremental changes can be user-configurable.

In operation 430, the computing system 110 can apply a function to each of the candidate implant parameter sets of the first set, to calculate a result of each candidate implant parameter set of the first set of candidate implant parameter sets. The result can include a gap curve representing a gap between the implant and a contacting surface of the joint. The gap can be represented at a plurality of points through a range of motion of the joint.

A first example function for executing operation 430 can evaluate the gap at each of the measured flexion positions for a configuration represented by the candidate implant parameter set, and perform a sum of the magnitudes (i.e. the mathematical "absolute values") of those gap spacings to determine a "total spacing" result. The first example function can be used to rank the candidate implant parameter sets with respect to an ideal gap curve, where the ideal gap curve would have zero or substantially zero positive gap or negative gap (i.e. overlap) of the implants in any position measured during the range of motion. The ideal gap curve with respect to the first example function implies that the implants are just barely touching, and that the articular motion of the postoperative joint is very similar to the preoperative joint. The "total spacing" for this parameter set would be zero. Ranking of parameter sets in this example would consider lower total spacings to be better than higher total spacings.

A second example function for executing operation 430 would have a result that includes the sum of the magnitudes of any positive gaps and doubled magnitudes of any negative gaps. The second example function would prefer positive gaps to negative gaps, thereby preferring a looser joint to a joint that would be tight due to overlap of the implants during the range of motion.

In operation 440, the computing system 110 can provide a graphical representation of the result according to at least one candidate implant parameter set of the first set of candidate implant parameter sets. The result can be provided within a surgical planning graphical user interface (GUI), and the result can include result identification information. For example, the computing system 110 can apply colors or other visual indicators such that a result can be visually correlated to user-interface elements that will lead to the corresponding result as described herein with respect to FIGS. 3A and 3B. In some embodiments, computing system 110 can implement operation 440 by applying an evaluation function to the first set of candidate implant parameter sets to determine a preferred candidate parameter set, and the computing system 110 can then provide, within the surgical planning GUI, a graphical indication corresponding to the preferred candidate parameter set. Embodiments are not limited to only one preferred candidate parameter set and more than one preferred candidate parameter set can be provided.

In operation 450, the computing system 110 can provide, within the surgical planning GUI, user interface controls to allow a user to execute incremental changes corresponding to candidate implant parameter sets of the first set of candidate implant parameter sets. Selecting at least one of the user interface controls implements the result of at least one candidate implant parameter set in the graphical representation. At least one of the user interface controls includes identification information correlating to result identification information for the result of the corresponding candidate implant parameter set.

In operation 460, the computing system 110 can receive a selection of a candidate implant parameter set of the first set of candidate implant parameter sets. The computing system 110 can receive the selection via the user interface controls. The selection can be based on a gap curve shape criterion as described herein regarding FIGS. 3A and 3B. Subsequent to receiving the selection, the computing system 110 can generate another set of one or more candidate implant parameter sets.

Though arranged serially in the example of FIG. 4, other examples can reorder the operations, omit one or more operations, and/or execute two or more operations in parallel using multiple processors or a single processor organized as two or more virtual machines or sub-processors. Moreover, still other examples can implement the operations as one or more specific interconnected hardware or integrated circuit modules with related control and data signals communicated between and through the modules. Thus, any process flow is applicable to software, firmware, hardware, and hybrid implementations.

Modules, Components and Logic

Certain embodiments of the computer systems described herein can include logic or a number of components, modules, or mechanisms. Modules can constitute either software modules (e.g., code embodied on a machine-readable medium or in a transmission signal) or hardware modules. A hardware module is a tangible unit capable of performing certain operations and can be configured or arranged in a certain manner. In example embodiments, one or more computer systems (e.g., a standalone, client or server computer system) or one or more hardware modules of a computer system (e.g., a processor or a group of processors) can be configured by software (e.g., an application or application portion) as a hardware module that operates to perform certain operations as described herein.

In various embodiments, a hardware module can be implemented mechanically or electronically. For example, a hardware module can comprise dedicated circuitry or logic that is permanently configured (e.g., as a special-purpose processor, such as a field programmable gate array (FPGA) or an application-specific integrated circuit (ASIC)) to perform certain operations. A hardware module can also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) can be driven by cost and time considerations.

Accordingly, the term "hardware module" should be understood to encompass a tangible entity, be that an entity that is physically constructed, permanently configured (e.g., hardwired) or temporarily configured (e.g., programmed) to operate in a certain manner and/or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor can be configured as respective different hardware modules at different times. Software can accordingly configure a processor, for example, to constitute a particular hardware module at one instance of time and to constitute a different hardware module at a different instance of time.

Hardware modules can provide information to, and receive information from, other hardware modules. Accordingly, the described hardware modules can be regarded as being communicatively coupled. Where multiple such hardware modules exist contemporaneously, communications can be achieved through signal transmission (e.g., over appropriate circuits and buses) that connect the hardware modules. In embodiments in which multiple hardware modules are configured or instantiated at different times, communications between such hardware modules can be achieved, for example, through the storage and retrieval of information in memory structures to which the multiple hardware modules have access. For example, one hardware module can perform an operation and store the output of that operation in a memory device to which it is communicatively coupled. A further hardware module can then later access the memory device to retrieve and process the stored output. Hardware modules can also initiate communications with input or output devices, and can operate on a resource (e.g., a collection of information).

The various operations of example methods described herein can be performed, at least partially, by one or more processors that are temporarily configured (e.g., by software) or permanently configured to perform the relevant operations. Whether temporarily or permanently configured, such processors can constitute processor-implemented modules that operate to perform one or more operations or functions. The modules referred to herein can, in some example embodiments, comprise processor-implemented modules.

Similarly, the methods described herein can be at least partially processor-implemented. For example, at least some of the operations of a method can be performed by one or more processors or processor-implemented modules. The performance of certain of the operations can be distributed among the one or more processors, not only residing within a single machine, but also deployed across a number of machines. In some example embodiments, the processor or processors can be located in a single location (e.g., within a home environment, an office environment or as a server farm), while in other embodiments the processors can be distributed across a number of locations.

The one or more processors can also operate to support performance of the relevant operations in a "cloud computing" environment or as a "software as a service" (SaaS). For example, at least some of the operations can be performed by a group of computers (as examples of machines including processors), with these operations being accessible via a network (e.g., the Internet) and via one or more appropriate interfaces (e.g., APIs).

Electronic Apparatus and System

Example embodiments can be implemented in digital electronic circuitry, in computer hardware, firmware, software, or in combinations of them. Example embodiments can be implemented using a computer program product, for example, a computer program tangibly embodied in an information carrier, for example, in a machine-readable medium for execution by, or to control the operation of, data processing apparatus, for example, a programmable processor, a computer, or multiple computers. Certain example embodiments of a computing system 110 (FIG. 1) can include a machine-readable medium storing executable instructions to be performed by the computing system 110.

A computer program can be written in any form of programming language, including compiled or interpreted languages, and it can be deployed in any form, including as a stand-alone program or as a module, subroutine, or other unit suitable for use in a computing environment. A computer program can be deployed to be executed on one computer or on multiple computers at one site or distributed across multiple sites and interconnected by a communication network.

In example embodiments, operations can be performed by one or more programmable processors executing a computer program to perform functions by operating on input data and generating output. Method operations can also be performed by, and apparatus of example embodiments can be implemented as, special purpose logic circuitry (e.g., a FPGA or an ASIC).

The computing system can include clients and servers. A client and server are generally remote from each other and typically interact through a communication network. The relationship of client and server arises by virtue of computer programs running on the respective computers and having a client-server relationship to each other. In embodiments deploying a programmable computing system, it will be appreciated that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware can be a design choice. Below are set out hardware (e.g., machine) and software architectures that can be deployed, in various example embodiments.

Example Machine Architecture and
Machine-Readable Medium

Figure 5:
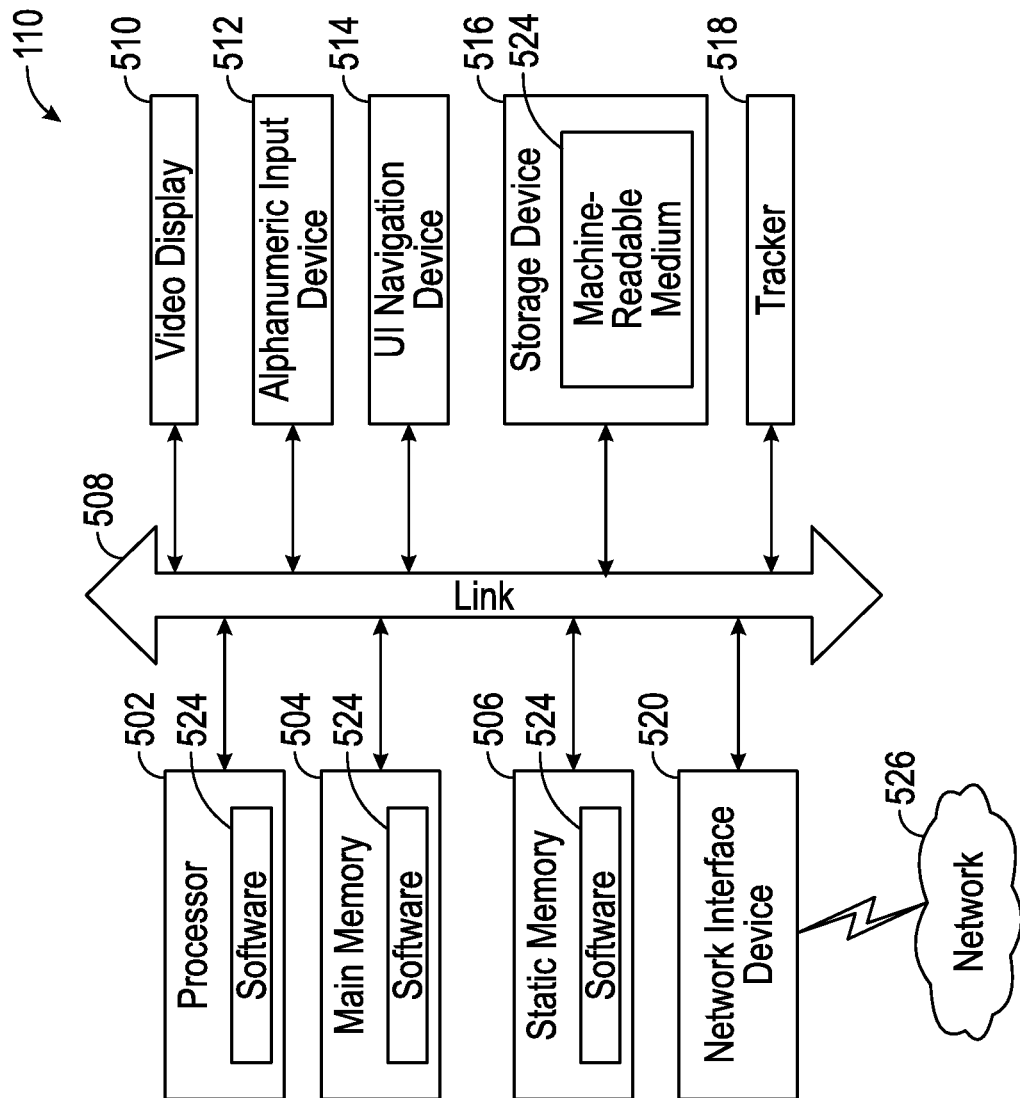
FIG. 5 is a diagrammatic representation of a machine in the example form of a computer system within which a set of instructions for causing the machine to perform any one or more of the methodologies discussed herein can be executed.

FIG. 5 is a block diagram of machine in the example form of a computer system 110 within which instructions, for causing the machine to perform any one or more of the methodologies discussed herein, can be executed. In alternative embodiments, the machine operates as a standalone device or can be connected (e.g., networked) to other machines. In a networked deployment, the machine can operate in the capacity of a server or a client machine in server-client network environment, or as a peer machine in a peer-to-peer (or distributed) network environment. The machine can be a personal computer (PC), a tablet PC, a set-top box (STB), a PDA, a cellular telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 110 includes a processor 502 (e.g., a central processing unit (CPU), a graphics processing unit (GPU) or both), a main memory 504 and a static memory 506, which communicate with each other via a bus 508. The computer system 110 can further include a video display unit 510 (e.g., a liquid crystal display (LCD) or a cathode ray tube (CRT)). The computer system 110 also includes an alphanumeric input device 512 (e.g., a keyboard), a user interface (UI) navigation device (or cursor control device) 514 (e.g., a mouse), a disk drive unit 516, trackers 518 or firmware for reading motion sensors such as, for example, sensors 120 (FIG. 1) or 220 (FIG. 2) and a network interface device 520.

The trackers can sense locations of anatomical structures in an implant host. The processor 502 can receive a first implant parameter set. The first implant parameter set will define parameters of a surgical plan. The surgical plan will have been generated using data collected while moving the joint through a range of motion. Examples of currently available trackers include optical tracking systems, such as the Polaris Spectra system (available from Northern Digital Incorporated, Ontario, Canada), or the electromagnetic tracking system Aurora (also available from Northern Digital Incorporated.). The Polaris Spectra tracks position and rotation of infrared-reflective arrays mounted to the patient's bones and surgical instruments using a stereo-camera video system. The Aurora senses position by sensing currents in coils that are attached to the patient and the surgical instruments, while a magnetic field transmitter modulates a magnetic field in proximity to the sensors. Both of these systems, and other similar systems, are currently available to provide the tracking capability in computer-assisted surgical systems. These systems can communicate with the computer system 110 using protocols such as USB (Universal Serial Bus) protocols.

The processor 502 can generate a first set of candidate implant parameter sets, wherein each candidate parameter set of the first set of candidate implant parameter sets is the result of an incremental change, relative to the first implant parameter set, to at least one parameter of the first parameter set. A candidate implant parameter set can include one or more of a size of an implant, a shape of the implant, an orientation of the implant, and a position of the implant relative to the joint The processor 502 can apply a function, as described regarding operation 430 of FIG. 4, to each of the candidate implant parameter sets of the first set of candidate implant parameter sets. Through use of this function, the processor 502 can calculate a result of each candidate implant parameter set of the first set of candidate implant parameter sets. The result can include a gap curve representing a gap between the implant and a contacting surface of the joint as described herein regarding FIGS. 3A and 3B.

The video display 510 can be arranged to present a graphical representation of the result according to at least one candidate implant parameter set of the first set of candidate implant parameter sets. The result can include result identification information similar to, for example, color-coding as described regarding FIGS. 3A and 3B.

The video display 510 can present user interface controls to allow a user to execute incremental changes corresponding to candidate implant parameter sets of the first set of candidate implant parameter sets. Selecting at least one of the user interface controls implements the result of at least one candidate implant parameter set in the graphical representation. At least one of the user interface controls includes identification information correlating to result identification information for the result of the corresponding candidate implant parameter set.

The video display 510 can be further arranged to receive a selection of a candidate implant parameter set. The processor 502 can be arranged to apply an evaluation function to the first set of candidate implant parameter sets to determine a preferred candidate parameter set. The video display 510 can provide a graphical indication corresponding to the preferred candidate parameter set. The processor 502 can provide a second set of one or more candidate movements based on the adjusted implant location.

Machine-Readable Medium

The disk drive unit 516 includes a machine-readable medium 522 on which is stored one or more sets of instructions and data structures (e.g., software) 524 embodying or used by any one or more of the methodologies or functions described herein. The instructions 524 can also reside, completely or at least partially, within the main memory 504, static memory 506, and/or within the processor 502 during execution thereof by the computer system 110, the main memory 504 and the processor 502 also constituting machine-readable media.

While the machine-readable medium 522 is shown in an example embodiment to be a single medium, the term "machine-readable medium" can include a single medium or multiple media (e.g., a centralized or distributed database, and/or associated caches and servers) that store the one or more instructions or data structures. The term "machine-readable medium" shall also be taken to include any tangible medium that is capable of storing, encoding or carrying instructions for execution by the machine and that cause the machine to perform any one or more of the methodologies of example embodiments, or that is capable of storing, encoding or carrying data structures used by or associated with such instructions. The term "machine-readable medium" shall accordingly be taken to include, but not be limited to, solid-state memories, and optical and magnetic media. Specific examples of machine-readable media include non-volatile memory, including by way of example, semiconductor memory devices (e.g., erasable programmable read-only memory (EPROM), electrically erasable programmable read-only memory (EEPROM), and flash memory devices; magnetic disks such as internal hard disks and removable disks; magneto-optical disks; and CD-ROM and DVD-ROM disks. A "machine-readable storage medium" shall also include devices that can be interpreted as transitory, such as register memory, processor cache, and RAM, among others. The definitions provided herein of machine-readable medium and machine-readable storage medium are applicable even if the machine-readable medium is further characterized as being "non-transitory." For example, any addition of "non-transitory," such as non-transitory machine-readable storage medium, is intended to continue to encompass register memory, processor cache, and RAM, among other memory devices.

Transmission Medium

The instructions 524 can further be transmitted or received over a communications network 526 using a transmission medium. The instructions 524 can be transmitted using the network interface device 520 and any one of a number of well-known transfer protocols (e.g., HTTP). Examples of communication networks include a LAN, a WAN, the Internet, mobile telephone networks, plain old telephone (POTS) networks, and wireless data networks (e.g., WiFi and WiMax networks). The term "transmission medium" shall be taken to include any intangible medium that is capable of storing, encoding, or carrying instructions for execution by the machine, and includes digital or analog communications signals or other intangible media to facilitate communication of such software.

Although an embodiment has been described with reference to specific example embodiments, it will be evident that various modifications and changes can be made to these embodiments. Accordingly, the specification and drawings are to be regarded in an illustrative rather than a restrictive sense. The accompanying drawings that form a part hereof, show by way of illustration, and not of limitation, specific embodiments in which the subject matter can be practiced. The embodiments illustrated are described in sufficient detail to enable those skilled in the art to practice the teachings disclosed herein. Other embodiments can be used and derived therefrom, such that structural and logical substitutions and changes can be made without departing from the scope of this disclosure. This Detailed Description, therefore, is not to be taken in a limiting sense, and the scope of various embodiments is defined only by the appended claims, along with the full range of equivalents to which such claims are entitled.

Although specific embodiments or examples have been illustrated and described herein, it should be appreciated that any arrangement calculated to achieve the same purpose can be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended; that is, a system, device, article, or process that includes elements in addition to those listed after such a term in a claim are still deemed to fall within the scope of that claim. Moreover, in the following claims, the terms "first," "second," "third," and so forth are used merely as labels, and are not intended to impose numerical requirements on their objects.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

We claim:

1. A method of determining a position of a surgical implant, the method comprising:
   providing a user interface on a display, the user interface comprising a plurality of views of a location of a virtual implant and a plurality of user controls for refining a position of the virtual implant, wherein the virtual implant corresponds to the surgical implant, wherein at least one of the plurality of views includes a mapping of a plurality of points creating a gap curve, wherein the gap curve indicates how a gap between a first bone and a second bone of a joint changes with each degree of flexion of the joint;
   receiving a user input pertaining to one of the plurality of user controls;
   updating the location of the virtual implant within the plurality of views and the mapping of the gap curve within the at least one view based on the received user input; and
   generating a surgical plan to place the surgical implant based on the updated location of the virtual implant.

2. The method of claim 1, wherein the plurality of user controls comprise one or more of a left input, a right input, a superior input, an inferior input, a posterior input, an anterior input, a clockwise input, and a counter-clockwise input.

3. The method of claim 1, wherein the plurality of user controls comprise a user control configured to select a type of virtual implant from a plurality of types of virtual implants.

4. The method of claim 1, further comprising:
   for at least two of the plurality of user controls, determining an updated mapping of the gap curve resulting from a selection of the user control; and
   displaying representations of the updated mappings of the gap curve in the user interface.

5. The method of claim 1, further comprising:
   for at least two of the plurality of user controls, determining an updated value of the gap curve resulting from a selection of the user control, and
   providing an indication in the user interface of a recommended user control based on the determined updated values.

6. The method of claim 1, further comprising:
   receiving location information pertaining to one or more positions of a joint of a patient as the joint is moved through a range of motion; and
   determining the mapping of the gap curve based at least in part on the one or more positions of the joint.

7. The method of claim 6, wherein determining the mapping of the gap curve is further based at least in part on the location of the virtual implant.

8. The method of claim 1, wherein:
   the first bone comprises a tibia;
   the second bone comprises a femur; and
   the implant comprises a tibial implant.

9. The method of claim 1, wherein:
the first bone comprises a tibia;
the second bone comprises a femur; and
the implant comprises a femoral implant.

10. A system for determining a position of a surgical implant, the system comprising:
a display;
a processor in operable communication with the display; and
a non-transitory, processor-readable storage medium in operable communication with the processor,
wherein the processor-readable storage medium contains one or more instructions that, when executed, cause the processor to:
provide a user interface on the display, the user interface comprising a plurality of views of a location of a virtual implant and a plurality of user controls for refining a position of the virtual implant, wherein the virtual implant corresponds to the surgical implant, wherein at least one of the plurality of views includes a mapping of a plurality of points creating a gap curve, wherein the gap curve indicates how a gap between a first bone and a second bone of a joint changes with each degree of flexion of the joint;
receive a user input pertaining to one of the plurality of user controls,
update the location of the virtual implant within the plurality of views and the mapping of the gap curve within the at least one view based on the received user input, and
generate a surgical plan to place the surgical implant based on the updated location of the virtual implant.

11. The system of claim 10, wherein the plurality of user controls comprise one or more of a left input, a right input, a superior input, an inferior input, a posterior input, an anterior input, a clockwise input, and a counter-clockwise input.

12. The system of claim 10, wherein the plurality of user controls comprise a user control configured to select a type of virtual implant from a plurality of types of virtual implants.

13. The system of claim 10, wherein the one or more instructions, when executed, further cause the processor to:
for at least two of the plurality of user controls, determine an updated mapping of the gap curve resulting from a selection of the user control; and
display representations of the updated mappings of the gap curve in the user interface.

14. The system of claim 10, wherein the one or more instructions, when executed, further cause the processor to:
for at least two of the plurality of user controls, determine an updated value for the gap curve resulting from a selection of the user control, and
provide an indication in the user interface of a recommended user control based on the determined updated values.

15. The system of claim 10, further comprising:
a tracking and navigation system in operable communication with the processor,
wherein the one or more instructions, when executed, further cause the processor to:
receive, from the tracking and navigation system, location information pertaining to one or more positions of a joint of a patient as the joint is moved through a range of motion, and
determine the mapping of the gap curve based at least in part on the one or more positions of the joint.

16. The system of claim 15, wherein determining the mapping of the gap curve is further based at least in part on the location of the virtual implant.

17. The system of claim 10, wherein:
the first bone comprises a tibia;
the second bone comprises a femur; and
the virtual implant comprises a tibial implant.

18. The system of claim 10, wherein:
the first bone comprises a tibia;
the second bone comprises a femur; and
the virtual implant comprises a femoral implant.

19. A non-transitory, processor-readable storage medium containing one or more instructions that, when executed, cause a processor to:
provide a user interface on a display, the user interface comprising a plurality of views of a location of a virtual implant and a plurality of user controls for refining a position of the virtual implant, wherein the virtual implant corresponds to the surgical implant, wherein at least one of the plurality of views includes a mapping of a mapping of a plurality of points creating a gap curve, wherein the gap curve indicates how a gap between a first bone and a second bone of a joint changes with each degree of flexion of the joint;
receive a user input pertaining to one of the plurality of user controls;
update the location of the virtual implant within the plurality of views and the mapping of the gap curve within the at least one view based on the received user input; and
generate a surgical plan to place the surgical implant based on the updated location of the virtual implant.

20. The storage medium of claim 19, wherein the one or more instructions, when executed, further cause the processor to:
for at least two of the plurality of user controls, determine an updated mapping of the gap curve resulting from a selection of the user control; and
display representations of the updated mappings of the gap curve in the user interface.

21. The storage medium of claim 19, wherein the one or more instructions, when executed, further cause the processor to:
for at least two of the plurality of user controls, determine an updated value for the gap curve resulting from a selection of the user control, and
provide an indication in the user interface of a recommended user control based on the determined updated values.

22. The storage medium of claim 19, wherein the one or more instructions, when executed, further cause the processor to:
receive, from a tracking and navigation system, location information pertaining to one or more positions of a joint of a patient as the joint is moved through a range of motion; and
determine the mapping of the gap curve based at least in part on the one or more positions of the joint.

* * * * *